United States Patent
Nguyen et al.

(10) Patent No.: US 8,697,143 B2
(45) Date of Patent: *Apr. 15, 2014

(54) HEAT ACTIVATED DURABLE STYLING COMPOSITIONS COMPRISING SACCHARIDE TYPE COMPOUNDS AND FILM FORMING AGENTS

(75) Inventors: Nghi Nguyen, Edison, NJ (US); David W. Cannell, Plainfield, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,423

(22) Filed: Feb. 24, 2012

(65) Prior Publication Data

US 2012/0213723 A1    Aug. 23, 2012

Related U.S. Application Data

(63) Continuation of application No. 10/532,317, filed as application No. PCT/IB02/04734 on Oct. 22, 2002, now abandoned.

(51) Int. Cl.
*A61K 33/04* (2006.01)
*A61K 8/73* (2006.01)

(52) U.S. Cl.
USPC ............................. 424/702; 424/70.13

(58) Field of Classification Search
USPC ....................... 424/70.7, 702, 70.13
See application file for complete search history.

(56) References Cited

U.S. PATENT DOCUMENTS

| | | | |
|---|---|---|---|
| 4,668,508 A | 5/1987 | Grollier et al. | |
| 4,845,204 A | 7/1989 | Lang et al. | |
| 4,900,545 A | 2/1990 | Wisotzki et al. | |
| 5,494,659 A | 2/1996 | Salka et al. | |
| 5,690,924 A | 11/1997 | Keil et al. | |
| 6,369,117 B1 | 4/2002 | Dubief et al. | |
| 2002/0031483 A1 | 3/2002 | Beck et al. | |

FOREIGN PATENT DOCUMENTS

| | | |
|---|---|---|
| CA | 2107120 | 9/1992 |
| EP | 0 403 282 | 12/1990 |
| JP | 2002-029945 | 1/1929 |
| JP | 62-501711 | 7/1987 |
| JP | 02-134312 | 5/1990 |
| JP | 03-063214 | 3/1991 |
| JP | 06-40853 | 2/1994 |
| JP | 06-100419 | 4/1994 |
| JP | 06-505973 | 7/1994 |
| JP | 08-020516 | 1/1996 |
| JP | 08-217645 | 8/1996 |
| JP | 09-501684 | 2/1997 |
| JP | 09-067234 | 3/1997 |
| JP | 2000-508373 | 7/2000 |
| JP | 2000-273029 | 10/2000 |
| JP | 2000-290143 | 10/2000 |
| JP | 2000-319145 | 11/2000 |
| JP | 2001-19626 | 1/2001 |
| JP | 2002-518423 | 6/2002 |
| JP | 2002-249413 | 9/2002 |
| WO | WO 98/31751 | 7/1998 |
| WO | WO 99/66888 | 12/1999 |
| WO | WO 00/67709 | 11/2000 |
| WO | WO 01/68040 | 9/2001 |
| WO | 02/078649 | 10/2002 |
| WO | 02/078655 | 10/2002 |
| WO | WO 02/078655 | 10/2002 |

OTHER PUBLICATIONS

BASF, Polymeric Luviquat Grades, Technical Information, May 1998, p. 1-16.

Decision dated Feb. 1, 2011 as received in the corresponding Japanese Application No. 2004-546221.

*Primary Examiner* — Blessing M Fubara
*Assistant Examiner* — Jennifer A Berrios
(74) *Attorney, Agent, or Firm* — Oblon, Spivak, McClelland, Maier & Neustadt, L.L.P.

(57) ABSTRACT

A composition for durable non-permanent shaping or durable retention of a non-permanent shape of least one keratinous fiber comprising:
(a) at least one film forming agent; and
(b) at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group.

13 Claims, No Drawings

HEAT ACTIVATED DURABLE STYLING COMPOSITIONS COMPRISING SACCHARIDE TYPE COMPOUNDS AND FILM FORMING AGENTS

This application is a continuation application of U.S. Ser. No. 10/532,317 filed May 12, 2006, abandoned, which was a National Stage of PCT/IB02/04734 filed Oct. 22, 2002.

The present invention relates to compositions, kits comprising these compositions, and methods for using these compositions for durable non-permanent shaping or for durable retention of a non-permanent shape of at least one keratinous fiber, including human keratinous fibers, by applying to the at least one keratinous fiber compositions which comprise at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group, and, in certain embodiments, at least one film forming agent different from the at least one compound, and heating the at least one keratinous fiber. These compositions may both impart a durable non-permanent shape to the at least one keratinous fiber and durably retain a non-permanent shape of the at least one keratinous fiber.

In today's market, many consumers prefer the flexibility of non-permanent hairstyles, that is, those styles obtained via non-permanent shaping of the hair. Typically, such non-permanent styles disappear when the hair is wetted, especially when the hair is washed with water and/or shampoo. Methods for non-permanent shaping of keratinous fibers include, for example, brushing, teasing, braiding, the use of hair rollers, and heat styling, optionally with a commercially available styling product. Non-limiting examples of heat styling include blow drying, crimping and curling methods using elevated temperatures (such as, for example, setting hair in curlers and heating, and curling with a curling iron and/or hot rollers).

While such compositions and methods may provide for non-permanent shaping of keratinous fibers, many consumers desire a higher degree of styling than most commercially available products and Methods employing these products provide. For example, many consumers desire compositions and methods that improve non-permanent curl formation. There is a need, therefore, for compositions and methods for non-permanent shaping of keratinous fibers that result in a higher degree of styling, such as non-permanent curl formation.

Further, many people desire compositions and methods for retaining a particular non-permanent shape or style of keratinous fibers such as hair. A common way to retain a particular hairstyle is with the use of a hairspray, typically applied after styling the hair. Other methods to retain a hairstyle or shape of keratinous fibers include the use of mousses, gels, and lotions. The materials in these compositions are generally film forming agents, resins, gums, and/or adhesive polymers.

While such compositions and methods may provide for non-permanent shaping of keratinous fibers, many consumers desire compositions and methods for durable retention of a particular non-permanent shape or style of keratinous fibers such as hair, such as, for example, those that hold or maintain a shape of a keratinous fiber until the keratinous fiber is washed with water and/or shampoo. Further, many consumers desire compositions and methods that allow hair to retain a particular shape longer than untreated hair, even after washing or shampooing the hair.

Thus, while commercially available compositions may provide temporary setting benefits, many consumers desire a higher level of retention or hold. Good holding power is one attribute a consumer looks for in styling products for keratinous fibers. Specifically, curl retention under conditions of changing humidity, for example changes to a higher humidity, is sought after by the consumer. Further, good curl retention in damaged hair is important to the consumer since the hair fiber has been weakened and will be less likely to maintain the curl. Therefore, there is also a need for methods for durably retaining a shape of keratinous fibers even under conditions of high humidity, such as at atmospheric humidity above 40%.

Sugars and sugar derivatives are one class of the countless number of compounds that have been added to hair care compositions. Documented uses of sugars in hair care compositions include: the use of glucose to improve the tactile and elastic properties of natural hair (Hollenberg and Mueller, *SOFW J.* 121(2) (1995)); the use of glucose for hair damage prophylaxis and damaged hair repair (Hollenberg & Matzik, *Seifen, Oele, Fette, Wachase* 117(1) (1991)); the use of glucose in shampoos (J04266812, assigned to Lion Corp.); the use of trehalose for moisture retention (J06122614, assigned to Shiseido Co. Ltd.); a composition for the lanthionization of hair comprising a sugar (U.S. Pat. Nos. 5,348,737 and 5,641,477, assigned to Avlon Ind. Inc.); the incorporation of xylobiose into cosmetic compositions to provide enhanced moisture retention and reduce excessive roughness and dryness of the skin and hair (U.S. Pat. No. 5,660,838, assigned to Suntory Ltd.); a composition for the regeneration of hair split-ends that contains at least one mono- or di-saccharide (U.S. Pat. No. 4,900,545, assigned to Henkel); hair care compositions to improve hair strength, hold and volume that contain $C_5$ to $C_6$ carbohydrates such as glucose; the use of fucose in a hair treatment to prevent split ends (DE29709853, assigned to Goldwell GMBH); and the use of saccharides in a shampoo to improve combing properties and control hair damage (J09059134, assigned to Mikuchi Sangyo KK).

In essence, sugars have been applied to hair for countless reasons from moisturizing to enhancing hair growth (J10279439, assigned to Kureha Chem. Ind. Co. Ltd.). Clearly, however, not all sugars are the same and not all sugars impart the same properties when applied to a keratinous fiber.

The inventors have envisaged the application to at least one keratinous fiber of at least one composition comprising at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group. In particular, the inventors have discovered that compositions and methods using these compositions comprising applying to the at least one keratinous fiber at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group, and heating the at least one keratinous fiber are useful for durable non-permanent shaping of at least one keratinous fiber or for durable retention of a non-permanent shape of at least one keratinous fiber.

Thus, to achieve at least one of these and other advantages, the present invention, in one aspect, provides a composition for durable non-permanent shaping of at least one keratinous fiber or durable retention of a non-permanent shape of at least one keratinous fiber comprising at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group, and at least one film forming agent different from the at least one compound, wherein the at least one compound and the at least one film forming agent are present in an amount effective to impart a durable non-permanent shape to the at least one keratinous fiber or to durably retain a non-permanent shape of the at least one keratinous fiber. In one embodiment, the composition is heat-activated.

In another embodiment, the present invention is drawn to a method for durable non-permanent shaping of at least one keratinous fiber or durable retention of a non-permanent shape of at least one keratinous fiber comprising applying to the at least one keratinous fiber (i) at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group and (ii) at least one film forming agent different from the at least one compound; and heating the at least one keratinous fiber, wherein the at least one compound and at least one film forming agent are present in an amount effective to impart a durable non-permanent shape to the at least one at least one keratinous fiber or to durably retain a non-permanent shape of the at least one keratinous fiber, and further wherein the composition is applied prior to or during heating.

The present invention, in another aspect, provides a composition for durable non-permanent shaping of at least one keratinous fiber or durable retention of a non-permanent shape of at least one keratinous fiber comprising at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group, wherein the at least one compound is present in an amount effective to impart a durable non- permanent shape to the at least one keratinous fiber or to durably retain a non-permanent shape of the at least one keratinous fiber. In one embodiment, the composition is heat-activated.

In another embodiment, the present invention is drawn to a method for durable non-permanent shaping of at least one keratinous fiber or durable retention of a non-permanent shape of at least one keratinous fiber comprising applying to the at least one keratinous fiber at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group; and heating the at least one keratinous fiber, wherein the at least one compound is present in an amount effective to impart a durable non-permanent shape to the at least one at least one keratinous fiber or to durably retain a non-permanent shape of the at least one keratinous fiber, and further wherein the composition is applied prior to or during heating.

In yet another embodiment, the present invention provides a kit for durable non-permanent shaping of at least one keratinous fiber or durable retention of a non-permanent shape of at least one keratinous fiber comprising at least one compartment, wherein a first compartment comprises a first composition comprising at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group. In one embodiment, at least one compartment comprises at least one additional sugar, different from the at least one compound, and in another embodiment, at least one compartment comprises at least one film forming agent.

Certain terms used herein are defined below:

"At least one" as used herein means one or more and thus includes individual components as well as mixtures/combinations.

"Durable retention of a shape" as used herein means that, following at least six shampoos after treatment, treated hair still retains the ability to retain a particular shape after styling as compared to the ability of untreated hair to retain a particular shape after styling.

"Durable shaping," as used herein, refers to holding or keeping a shape of a keratinous fiber until the keratinous fiber is washed with water and/or shampoo. Retention of a shape can be evaluated by measuring, and comparing, the ability to retain a curl under conditions of high relative humidity of the treated hair arid of the untreated hair in terms of Curl Efficiency (for example, see Examples 1 and 2).

"Heating" refers to the use of elevated temperature (i.e., above 100° C.). In one embodiment, the heating in the inventive method may be provided by directly contacting the at least one keratinous fiber with a heat source, e.g., by heat styling of the at least one keratinous fiber. Non-limiting examples of heat styling by direct contact with the at least one keratinous fiber include flat ironing, and curling methods using elevated temperatures (such as, for example, setting hair in curlers and heating, and curling with a curling iron and/or hot rollers). In another embodiment, the heating in the inventive method may be provided by heating the at least one keratinous fiber with a heat source which may not directly contact the at least one keratinous fiber. Non-limiting examples of heat sources which may not directly contact the at least one keratinous fiber include blow dryers, hood dryers, heating caps and steamers.

"A heat-activated" composition, as used herein, refers to a composition which, for example, shapes the at least one keratinous fiber better than the same composition which is not heated during or after application of the composition. Another example includes composition which retains a shape of at least one keratinous fiber better than the same composition which is not heated during or after application.

"High humidity" as defined herein refers to atmospheric humidity above 40%.

"Keratinous fibers" as defined herein may be human keratinous fibers, and may be chosen from, for example, hair.

"Non-permanent shaping" of keratinous fibers, as used herein, refers to a method of setting keratinous fibers in a particular shape or style which does not comprise breaking and reforming disulfide bonds within a keratinous fiber.

"Non-permanent shape" of keratinous fibers, as used herein, refers a shape or style of keratinous fibers obtained without breaking and reforming disulfide bonds within a keratinous fiber.

"Oligosaccharides" as defined herein refers to compounds generally comprising from two to ten monosaccharide units, which may be identical or different, bonded together.

"Polysaccharides" as defined herein refers to compounds generally comprising greater than ten monosaccharide units, which may be identical or different, bonded together.

"Polymers" as defined herein comprise copolymers (including terpolymers) and homopolymers.

It is to be understood that both the foregoing general description and the following detailed description are exemplary and explanatory only and are not restrictive of the invention, as claimed. Reference will now be made in detail to exemplary embodiments of the present invention.

As described above, sugars have been used in hair care compositions and other treatments for their moisture retaining properties. However, it was unexpectedly discovered by the present inventors that, in addition to retaining moisture, a certain class of sugars imparted a durable non-permanent shape or durable retention of a non-permanent shape or style to at least one keratinous fiber. In particular with respect to hair, saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group were found to impart good curl formation to the at least one keratinous fiber, and to prevent such curls from drooping, for example, due to humidity. Further, these compounds may impart to the at least one keratinous fiber an ability to retain a particular style even after shampooing the at least one keratinous fiber subsequent to treatment with a composition comprising at least one such compound. This is particularly true when the compounds are applied to the hair, and then the hair is heated.

Thus, the invention provides compositions for durable non-permanent shaping of at least one keratinous fiber or durable retention of a non-permanent shape of at least one keratinous fiber comprising (i) at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group and, optionally, (ii) at least one film forming agent, wherein the at least one compound and, optionally, the at least one film forming agent are present in an amount effective either to impart a durable non-permanent shape to the at least one keratinous fiber or to durably retain a non- permanent shape of the at least one keratinous fiber, depending on the embodiment. In one embodiment, the composition is heat-activated. In another embodiment, the composition both imparts a durable non-permanent shape to the at least one keratinous fiber and durably retains a non-permanent shape of the at least one keratinous fiber. The composition may further comprise at least one additional sugar.

The present invention also provides methods for durable non-permanent shaping of at least one keratinous fiber or for durable retention of a non-permanent shape of at least one keratinous fiber comprising applying to the at least one keratinous fiber a composition comprising (i) at least one saccharide type compound chosen from $C_3$ to $C_5$ monosaccharides, optionally substituted with at least one $C_1$ to $C_{22}$ carbon chain, and compounds comprising at least one $C_5$ to $C_7$ saccharide unit substituted with at least one amino group, (ii) at least one film forming agent; and heating the at least one keratinous fiber. The composition may be applied prior to or during heating. Further, the at least one compound and, optionally, the at least one film forming agent are present in an amount effective either to impart a durable non-permanent shape to the at least one keratinous fiber or to durably retain a non-permanent shape of the at least one keratinous fiber, depending on the embodiment. In one embodiment, the composition both imparts a durable non-permanent shape to the at least one keratinous fiber and durably retains a non-permanent shape of the at least one keratinous fiber. The composition may further comprise at least one additional sugar.

According to certain embodiments of the present invention, the at least one compound may be used in conjunction with at least one film-forming agent, such as, for example, film forming polymers and resins. For example, the film forming polymers may be chosen from cationic polymers, anionic polymers and nonionic polymers. Non-limiting examples of the at least one film forming agent are those listed at pages 1744 to 1747 of the CTFA International Cosmetic Ingredient Dictionary, $8^{th}$ edition (2000). In one embodiment, the at least one film forming agent may be chosen from water soluble compounds, oil soluble compounds and compounds soluble in organic solvents. According to the present invention, the at least one film forming agent may be present in an amount generally ranging from 0.01% to 30% of active material by weight relative to the total weight of the composition, such as from 0.1% to 10% of active material by weight. One of ordinary skill in the art will recognize that the at least one film forming agent according to the present invention may be commercially available, and may come from suppliers in the form of a dilute solution. The amounts of the at least one film forming agent disclosed herein therefore reflect the weight percent of active material.

Non-limiting examples of the at least one film forming agent are those disclosed in WO 01/18096, the disclosure of which is incorporated herein by reference. Other non-limiting examples of the at least one film forming agent include copolymers derived from (i) at least one vinyl monomer comprising at least one quaternary ammonium group and (ii) at least one additional monomer chosen from acrylamide, methacrylamide, alkyl acrylamides, dialkyl acrylamides, alkyl methacrylamides, dialkyl methacrylamides, alkyl acrylate, alkyl methacrylate, vinyl caprolactone, vinyl pyrrolidone, vinyl esters, vinyl alcohol, maleic anhydride, propylene glycol, and ethylene glycol.

Further non-limiting examples of the at least one film forming agent include:—vinyl acetate/vinyl tert butylbenzoate/ crotonic acid terpolymers such as those described in U.S. Pat. No. 4,282,203, the disclosure of which is incorporated herein by reference;

N-octylacrylamide/methyl methacrylate/hydroxypropyl methacrylate/acrylic acid/tert-butylamino-ethyl methacrylate copolymers such as those sold by NATIONAL STARCH under the name "AMPHOMER LV-71";

corn starch/polyvinylpyrrolidone copolymers such as Corn Starch Modified sold by National Starch and Chemicals under the name Amaize®;

vinylpyrrolidone/vinyl acetate copolymers such as those sold by BASF under the name "LUVISKOL VA 64 Powder";

vinyl acetate/crotonic acid/vinyl neodecanoate terpolymers such as those sold by NATIONAL STARCH under the name "RESYN® 28-2930";

acrylic acid/ethyl acrylate/N-tert-butylacrylamide terpolymers such as those sold by BASF under the name "ULTRA-HOLD 8";

acrylic acid/acrylates/hydroxyacrylates/succinic acid copolymers such as Acrylates/C1-2 succinates hydroxyacrylates copolymer sold by ISP as ALLIANZ LT-120;

vinyl acetate/crotonic acid (90/10) copolymers such as those sold by BASF under the name "LUVISET CA 66";

acrylic acid/methacrylic acid/acrylates/methacrylates copolymers such as Acrylates Copolymer sold by Amerchol Corp. (Edison, N.J., USA); and vinylcaprolactam/vinylpyrrolidone/dimethylamino ethyl methacrylate copolymers such as those sold by GAF under the name "POLYMER ACP-1018".

Further non-limiting examples of the at least one film forming agent include:

copolymers derived from (i) 1-vinyl-2-pyrrolidone and (ii) 1-vinyl-3-methylimidazolium salt (CTFA designation: polyquaternium-16), which is commercially available from BASF Corporation under the LUVIQUAT tradename (e.g., LUVIQUAT FC 370);

copolymers derived from reaction of (i) vinylcaprolactam and (ii) vinylpyrroldone with methylvinylimidazolium methosulfate, (CTFA designation: polyquaternium-46), which is commercially available from BASF;

copolymers derived from (i) vinylpyrrolidone and (ii) quaternized imidazoline monomers (CTFA designation: polyquaternium-44), which is commercially available from BASF;

copolymers derived from (i) 1-vinyl-2-pyrrolidone and (ii) 1-vinyl-3-methylimidazolium salt (CTFA designation: polyquaternium-16), which is commercially available from BASF Corporation under the LUVIQUAT tradename (e.g., LUVIQUAT FC 370);

poly(vinylamine), optionally quaternized;

poly-4-vinyl pyridine, optionally quaternized;

poly(ethyleneimine), optionally quaternized;

dimethyldiallylammonium chloride homopolymer (CTFA designation: polyquaternium-6);

copolymers derived from (i) acrylamide and (ii) dimethyldiallylammonium chloride (CTFA designation: polyquaternium-7);

copolymers derived from (i) dimethyldiallylammonium chloride and (ii) sodium acrylate (CTFA designation: Polyquaternium-22); and terpolymers derived from (i) dimethyldiallylammonium chloride, (ii) acrylic amide and (iii) sodium acrylate (CTFA designation: Polyquaternium-39).

Other non-limiting examples of the at least one film forming agent include derivatives of polysaccharide polymers such as cationic cellulose derivatives, for example, cationic cellulose, which is available from Amerchol Corp. (Edison, N.J., USA) in their Polymer JR™, LR™ and SR™ series of polymers, as salts of hydroxyethyl cellulose reacted with trimethyl ammonium substituted epoxide (CTFA designation: polyquaternium-10); polymeric quaternary ammonium salts of hydroxyethyl cellulose reacted with lauryl dimethyl ammonium-substituted epoxide (CTFA designation: polyquaternium-24), which is available from Amerchol Corp. (Edison, N.J., USA) under the tradename Polymer LM-200™; and cationic starch and derivatives thereof, such as quaternary starch, which is available from Croda.

In one embodiment, the at least one film forming agent is chosen from cationic polymers such as polyquaternium-16, polyquaternium-46, and polyquaternium-44. In another embodiment, the at least one film forming agent is chosen from nonionic polymers such as polymers derived from (1) corn starch and (2) polyvinylpyrrolidone; and copolymers derived from (1) vinyl acetate and (2) vinylpyrrolidone. In yet another embodiment, the at least one film forming agent is chosen from anionic polymers such as polymers derived from (1) vinyl acetate, (2) crotonic acid and (3) vinyl neodecanoate, polymers derived from (1) acrylic acid, (2) acrylates, (3) hydroxyacrylates and (4) succinic acid, and polymers derived from at least two monomers chosen from acrylic acid, methacrylic acid, esters of acrylic acid and esters of methacrylic acid. The at least one film forming agent chosen from anionic polymers can be neutralized in order to render the anionic polymers soluble.

The $C_3$ to $C_5$ monosaccharides according to the present invention may be chosen from any triose, tetrose and pentose. Further, the $C_3$ to $C_5$ monosaccharides can be chosen from the D-form, L-form and mixtures of any of the foregoing. Non-limiting examples of $C_3$ to $C_5$ monosaccharides include aldopentoses (such as xylose, arabinose, lyxose, and ribose), ketopentoses (such as ribulose and xylulose), aldotetroses (such as erythrose and treose), ketotetroses (such as erythrulose), aldotrioses (such as glyceraldehyde) and ketotrioses (such as dihydroxyacetone). The $C_3$ to $C_5$ monosaccharides may be chosen from $C_3$ to $C_5$ monosaccharides comprising aldehyde groups (aldoses), furanoses and other ring structures. The $C_3$ to $C_5$ monosaccharides may be further substituted with at least one group different from the $C_1$ to $C_{22}$ carbon chain.

Derivatives of $C_3$ to $C_5$ monosaccharides substituted with at least one $C_1$ to $C_{22}$ carbon chain may be used as the at least one compound of the present invention. For example, ammonias or primary amines may react with the aldehyde or ketone group of a sugar to form an imine derivative (i.e., a compound containing the functional group C=N). These imine compounds are sometimes also referred to as Schiff bases. Other non-limiting examples of derivatives of $C_3$ to $C_5$ monosaccharides are hemiacetal derivatives of $C_3$ to $C_5$ monosaccharides, hemiketal derivatives of $C_3$ to $C_5$ monosaccharides and any oxidized derivatives of $C_3$ to $C_5$ monosaccharides. These derivatives may be formed, for example, from the reaction of the aldehyde or ketone group of a sugar with an alcohol. Other exemplary derivatives of $C_3$ to $C_5$ monosaccharides may also include, but are not limited to, oligosaccharides derived from $C_3$ to $C_5$ monosaccharides, such as xylobiose. As previously mentioned, the at least one compound chosen from $C_3$ to $C_5$ monosaccharides substituted with at least one $C_1$ to $C_{22}$ carbon chain may be further substituted with at least one group different from the at least one $C_1$ to $C_{22}$ carbon chain. Thus, in one embodiment, the derivatives of $C_3$ to $C_5$ monosaccharides may be further substituted with at least one group different from the at least one $C_1$ to $C_{22}$ carbon chain.

According to the present invention, the at least one $C_1$ to $C_{22}$ carbon chain may be chosen from linear, branched and cyclic $C_1$ to $C_{22}$ carbon chains, which are saturated or unsaturated. The at least one $C_1$ to $C_{22}$ carbon chain may optionally be substituted. In one embodiment, the at least one $C_1$ to $C_{22}$ carbon chain is chosen from $C_{16}$ to $C_{18}$ carbon chains. In another embodiment, the at least one $C_1$ to $C_{22}$ carbon chain is chosen from $C_{16}$ carbon chains and $C_{18}$ carbon chains. Non-limiting examples of $C_{16}$ carbon chains are linear hexadecyl chains, and non-limiting examples of $C_{18}$ carbon chains are linear octadecyl chains.

Further, the $C_3$ to $C_5$ monosaccharides may be substituted with the at least one $C_1$ to $C_{22}$ carbon chain at any position on the sugar. For example, in one embodiment, a $C_3$ to $C_5$ monosaccharide is substituted with at least one $C_1$ to $C_{22}$ carbon chain at the $C_1$ position of the $C_3$ to $C_5$ monosaccharide. In another embodiment, a $C_3$ to $C_5$ monosaccharide is substituted with the at least one $C_1$ to $C_{22}$ carbon chain at at least one of the hydroxyl groups of the $C_3$ to $C_5$ monosaccharide. As used herein, substituted at at least one of the hydroxyl groups of a $C_3$ to $C_5$ monosaccharide means at least one of substitution on the hydroxyl group itself (i.e., formation of an ether linkage between the $C_3$ to $C_5$ monosaccharide and the $C_1$ to $C_{22}$ carbon chain) and substitution on the carbon atom to which the hydroxyl group is commonly bonded. Further, the $C_3$ to $C_5$ monosaccharides may be substituted with the at least one $C_1$ to $C_{22}$ carbon chain at a carbon atom bearing no hydroxyl groups (i.e., a $CH_2$ within the $C_3$ to $C_5$ monosaccharide or a carbon atom within the $C_3$ to $C_5$ monosaccharide bearing substituents other than a hydroxyl group). Further, the $C_3$ to $C_5$ monosaccharides may be further substituted with at least one substituent different from the at least one $C_1$ to $C_{22}$ carbon chain.

In one embodiment, the at least one film forming agent is chosen from cationic polymers such as polyquaternium-16, polyquaternium-46, and polyquaternium-44. In another embodiment, the at least one film forming agent is chosen from nonionic polymers such as polymers derived from (1) corn starch and (2) polyvinylpyrrolidone; and copolymers derived from (1) vinyl acetate and (2) vinylpyrrolidone. In yet another embodiment, the at least one film forming agent is chosen from anionic polymers such as polymers derived from (1) vinyl acetate, (2) crotonic acid and (3) vinyl neodecanoate, polymers derived from (1) acrylic acid, (2) acrylates, (3) hydroxyacrylates and (4) succinic acid, and polymers derived from at least two monomers chosen from acrylic acid, methacrylic acid, esters of acrylic acid and esters of methacrylic acid. The at least one film forming agent chosen from anionic polymers can be neutralized in order to render the anionic polymers soluble.

The at least one $C_5$ to $C_7$ saccharide unit according to the present invention may be chosen from any pentose, hexose and heptose. Further, the at least one $C_5$ to $C_7$ saccharide unit can be chosen from the D-form, L-form and mixtures of any of the foregoing. Non-limiting examples of $C_5$ to $C_7$ saccharide units are aldopentoses (such as xylose, arabinose, lyxose, and ribose), ketopentoses (such as ribulose and xylulose), aldohexoses (such as glucose and galactose), ketohexoses (such as fructose and sorbose), and heptoses (such as aldoheptoses and ketoheptoses, e.g., galactoheptulose and glucoheptulose). The at least one $C_5$ to $C_7$ saccharide unit may be chosen from those comprising aldehyde groups (aldoses), furanoses and other ring structures. The at least one $C_5$ to $C_7$ saccharide unit may be further substituted with at least one group different from the at least one amino group.

Derivatives of $C_5$ to $C_7$ saccharide units may also be used as the at least one $C_5$ to $C_7$ saccharide unit in the present invention. For example, ammonias or primary amines may react with the aldehyde or ketone group of a saccharide unit to form an imine derivative (i.e., a compound containing the functional group C=N). These imine compounds are sometimes also referred to as Schiff bases. Other non-limiting examples of derivatives of $C_5$ to $C_7$ saccharide units are hemiacetal derivatives of $C_5$ to $C_7$ saccharide units, hemiketal derivatives of $C_5$ to $C_7$ saccharide units and any oxidized derivatives of $C_5$ to $C_7$ saccharide units. These derivatives may be formed, for example, from the reaction of the aldehyde or ketone group of a saccharide unit with an alcohol. As previously mentioned, the at least one $C_5$ to $C_7$ saccharide unit may be further substituted with at least one group different from the at least one amino group. Thus, in one embodiment, the derivatives of $C_5$ to $C_7$ saccharide units may be further substituted with at least one group different from the at least one amino group.

According to the present invention, the at least one amino group may be chosen from substituted and unsubstituted amino groups. For example, the at least one amino group may be chosen from N-acetyl amino groups.

Further, the at least one $C_5$ to $C_7$ saccharide unit may be substituted with the at least one amino group at any position on the saccharide unit. For example, in one embodiment, the at least one $C_5$ to $C_7$ saccharide unit is substituted with the at least one amino group at the C1 position of the at least one $C_5$ to $C_7$ saccharide unit. In another embodiment, the at least one $C_5$ to $C_7$ saccharide unit is substituted with the at least one amino group at the C2 position of the at least one $C_5$ to $C_7$ saccharide unit.

Non-limiting examples of the at least one compound include $C_5$ monosaccharides substituted with at least one amino group, $C_6$ monosaccharides substituted with at least one amino group, $C_7$ monosaccharides substituted with at least one amino group, polymers comprising at least one $C_5$ monosaccharide substituted with at least one amino group, polymers comprising at least one $C_6$ monosaccharide substituted with at least one amino group, polymers comprising at least one $C_7$ monosaccharide substituted with at least one amino group, and glycoproteins comprising at least one $C_5$ to $C_7$ saccharide unit substituted with at least one amino group. In one embodiment, the at least one compound is chosen from oligosaccharides derived from the at least one $C_5$ to $C_7$ saccharide unit substituted with at least one amino group which may be further substituted with at least one group different from the at least one amino group.

Non-limiting examples of $C_5$ monosaccharides substituted with at least one amino group are pentosamines. In one embodiment, the pentosamines are chosen from aldopentosamines and ketopentosamines (such as xylosamine, arabinosamine, lyxosamine, ribosamine, ribulosamine and xylulosamine).

Non-limiting examples of $C_6$ monosaccharides substituted with at least one amino group include hexosamines (such as aldohexosamines and ketohexosamines). In one embodiment, for example, the hexosamines are chosen from glucosamine, galactosamine, allosamine, altrosamine, mannosamine, gulosamine, idosamine, galactosamine, and talosamine. In another embodiment, the at least one compound is glucosamine, and in another embodiment, is galactosamine.

Non-limiting examples of $C_7$ monosaccharides substituted with at least one amino group are heptosamines. For example, heptosamines may be chosen from aldoheptosamines and ketoheptosamines.

According to the present invention, the at least one saccharide type compound is present in the composition in an amount generally ranging from 0.01% to 10% by weight relative to the total weight of the composition, such as from 0.1% to 5% by weight.

The compositions of the present invention as well as those of the inventive methods may further comprise at least one additional sugar which is different from the at least one compound chosen from $C_3$ to $C_5$ monosaccharides substituted with at least one $C_1$ to $C_{22}$ carbon chain. The at least one additional sugar may, for example, aid in moisture retention. The effectiveness of a sugar in aiding in moisture retention may be measured by monitoring a DSC peak at a temperature ranging from 75° C. to 200° C.

The at least one additional sugar may be chosen from any sugar, carbohydrate and carbohydrate moiety. Non-limiting examples of the at least one additional sugar are monosaccharides, which include, but are not limited to, three to seven carbon sugars such as pentoses (for example, ribose, arabinose, xylose, lyxose, ribulose, and xylulose) and hexoses (for example, allose, altrose, glucose, mannose, gulose, idose, galactose, talose, sorbose, pstcose, fructose, and tagatose); oligosaccharides such as disaccharides (such as maltose, sucrose, cellobiose, trehalose and lactose); and polysaccharides such as starch, dextrins, cellulose and glycogen. In one embodiment, the at least one additional sugar of the invention are chosen from any aldoses and ketoses.

Further, the at least one additional sugar may be substituted or unsubstituted. For example, the at least one additional sugar may be substituted with at least one $C_1$ to $C_{22}$ carbon chain. In one embodiment, the at least one $C_1$ to $C_{22}$ carbon chain is chosen from linear, branched and cyclic $C_1$ to $C_{22}$ carbon chains, which are saturated or unsaturated. For example, the at least one $C_1$ to $C_{22}$ carbon chain may be chosen from $C_{16}$ to $C_{18}$ carbon chains (such as $C_{16}$ carbon chains and $C_{18}$ carbon chains). Further, for example, $C_{16}$ carbon chains may be chosen from linear hexadecyl chains and $C_{18}$ carbon chains may be chosen from linear octadecyl chains. In one embodiment, the at least one additional sugar is substituted with at least one $C_1$ to $C_{22}$ carbon chain at the C1 position of the at least additional one sugar.

According to the present invention, the at least one additional sugar is present in the composition in an amount generally ranging from 0.01% to 10% by weight relative to the total weight of the composition, such as from 0.1% to 5% by weight.

The compositions of the present invention as well as those of the inventive methods may be in the form of a liquid, an oil, a paste, a stick, a dispersion, an emulsion, a lotion, a gel, or a cream. Further, these compositions may further comprise at least one suitable additive chosen from additives commonly used in compositions for keratinous fibers. Non-limiting examples of the at least one suitable additive include anionic surfactants, cationic surfactants, nonionic surfactants, amphoteric surfactants, fragrances, penetrating agents, antioxidants, sequestering agents, opacifying agents, solubilizing agents, emollients, colorants, screening agents (such as sunscreens and UV filters), preserving agents, proteins, vitamins, silicones, polymers such as thickening polymers, plant oils, mineral oils, synthetic oils and any other additive conventionally used in compositions for the care and/or treatment of keratinous fibers. Needless to say, a person skilled in the art will take care to select the at least one suitable additive such that the advantageous properties of the composition in accordance with the invention are not, or are not substantially, adversely affected by the addition(s) envisaged.

The compositions of the present invention and those used in the methods of the present invention may also be provided as one-part compositions comprising at least one compound chosen from $C_3$ to $C_5$ monosaccharides substituted with at least one $C_1$ to $C_{22}$ carbon chain and, optionally, at least one additional sugar, and further, optionally at least one film forming agent, or in the form of a multi-component treatment or kit. The skilled artisan, based on the stability of the composition and the application envisaged, will be able to determine how the composition and/or multicomponent compositions should be stored and mixed. For example, simple sugars such as $C_3$ to $C_5$ monosaccharides are known to be stable at pH levels ranging from 4 to 9. In compositions where the pH range is below or above these levels, the sugars would be stored separately and added to the composition only at the time of application.

Thus, the present invention also relates to a kit for durable non-permanent shaping of at least one keratinous fiber or for durable retention of a non-permanent shape of at least one keratinous fiber comprising at least one compartment, wherein a first compartment comprises a first composition comprising at least one compound chosen from $C_3$ to $C_5$ monosaccharides substituted with at least one $C_1$ to $C_{22}$ carbon chain. In one embodiment, the first composition further comprises at least one additional sugar, different from the at least one compound, while in another embodiment, the first composition further comprises at least one film forming agent.

According to one aspect of the invention, the at least one compound suitable for the present invention is a mixture of pentoses substituted with at least one $C_1$ to $C_{22}$ carbon chain. XYLIANCE brand modified pentoses is a blend of hexadecyl glycosides and octadecyl glycosides wherein the glycosides comprise D-xylosides, L-arabinosides, and D-glucosides. XYLIANCE may be obtained from Soliance, Route de Bazancourt—51110 Pomacle, France.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters seating forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

EXAMPLES 1 AND 2

Unless otherwise noted, the following procedure was used in the following examples to determine the efficiency of $C_3$ to $C_5$ monosaccharides substituted with at least one $C_1$ to $C_{22}$ carbon chain. Hair swatches (2 g., 6.5-7.5 in.) were treated with a solution of film former/XYLIANCE (0.5 g solution/g of hair) then blow dried. The hair swatches were then styled with a curling iron for 1 minute and the curly swatches were placed in a humidity chamber at 90% relative humidity for 1 hour.

The Curl Efficiency was calculated as:

$$L_t/L_o \times 100$$

Where:
$L_o$ represents the original length of fully extended hair
$L_t$ represents the length of the hair after 1 hour in the humidity chamber
A lower Curl Efficiency represents a better curl retention.

EXAMPLE 1

Curl Efficiency of XYLIANCE and Film Former

Hair was treated as described above with styling solutions that contain 3% of Octylacrylamide/Acrylates/Butylaminoethyl/Methacrylate Copolymer (AMPHOMER LV-71 from National Starch and Chemicals Co.), and varying amounts of XYLIANICE. The results are shown in Table 1.

TABLE 1

Curl Efficiency of Hair Treated with Amphomer LV-71 and XYLIANCE

| Styling Solution | Curl Efficiency |
| --- | --- |
| 3% Amphomer LV-71/0% XYLIANCE | 76 |
| 3% Amphomer LV-71/0.1% XYLIANCE | 72 |
| 3% Amphomer LV-71/0.5% XYLIANCE | 61 |
| 3% Amphomer LV-71/1% XYLIANCE | 60 |

The data indicates that XYLIANCE improved the curl efficiency of hair that was treated with styling polymer.

EXAMPLE 2

Effects of Xyliance and Neutralized Film Former

Hair was treated as described above with solutions of 0.5% XYLIANCE and 6% Amphomer LV-71 that had been neutralized with AMP at various degrees of neutralization. The results are shown in Table 2.

TABLE 2

Curl Efficiency of Hair Treated with 0.5% XYLIANCE and 6% Amphomer LV-71 with Various Degrees of Neutralization

| Degree of Neutralization | Curl Efficiency |
| --- | --- |
| 0% Neutralization/0% XYLIANCE | 84 |
| 0% Neutralization/0.5% XYLIANCE | 73 |
| 40% Neutralization/0% XYLIANCE | 67 |
| 40% Neutralization/0.5% XYLIANCE | 57 |
| 80% Neutralization/0% XYLIANCE | 63 |
| 80% Neutralization/0.5% XYLIANCE | 59 |
| 100% Neutralization/0% XYLIANCE | 59 |
| 100% Neutralization/0.5% XYLIANCE | 56 |

The data indicate that XYLIANCE improved the curl retention of hair that was heat treated with styling polymer with various degrees of neutralization.

EXAMPLE 3

The following procedure was used to treat the hair and measure the Curl Droop: Hair swatches (2 g., 6.5-7.5 in.) were treated with an ethanol solution containing 6% Resyn® 28-2930 (neutralized to 85% with AMP) and 1% Xyliance (0.5 g solution/g of hair) then blow dried. The hair swatches were then heated with a flat iron for 1 minute and then shampooed with 10% sodium laureth sulfate (SLES). The treatment was repeated up to 6 times, as indicated. The treated hair swatches were shampooed 2, 4, and 6 times, then styled with a curling iron for 30 seconds and placed in a humidity chamber at 90% relative humidity to measure the Curl Droop. As the curl slowly relaxed in the humidity chamber, the length of the hair swatches was measured every minute (up to 15 minutes).

The Curl Droop was calculated as:

$$[(L_o-L_t)/(L_o-L_i)]\times 100$$

Where:
$L_o$ represents the original length of fully extended hair
$L_t$ represents the length of the hair at time t in the humidity chamber
$L_i$ represents the initial length of the hair at time 0 in the humidity chamber (i.e., after styling with a curling iron for 30 seconds)
A higher Curl Droop represents a better curl retention.

TABLE 1

Curl Droop of Hair Treated with Corn Starch Modified

| Solution Comprising 6% (active) Resyn ® 28-2930 (85% neutralized) | 0 minutes | 5 minutes | 10 minutes | 15 minutes |
|---|---|---|---|---|
| Without Xyliance, after treatment | 100 | 94 | 86 | 75 |
| With Xyliance, after treatment | 100 | 95 | 89 | 77 |
| Without Xyliance, after 2 shampoos | 100 | 91 | 83 | 71 |
| With glucosamine, after 2 shampoos | 100 | 93 | 86 | 72 |
| Without glucosamine, after 4 shampoos | 100 | 90 | 75 | 57 |
| With glucosamine, after 4 shampoos | 100 | 91 | 78 | 65 |
| Without glucosamine, after 6 shampoos | 100 | 59 | 45 | 27 |
| With glucosamine, after 6 shampoos | 100 | 88 | 75 | 57 |

The data showed that hair treated with at least one film forming agent (Resyn® 28-2930 (neutralized to 85% with AMP)), at least one compound chosen from $C_3$ to $C_5$ monosaccharides substituted with at least one $C_1$ to $C_{22}$ carbon chain (Xyliance) and heat had a higher curl retention than hair treated with at least one film forming agent (Resyn® 28-2930 (neutralized to 85% with AMP)) and heat but without at least one compound chosen from $C_3$ to $C_5$ monosaccharides substituted with at least one $C_1$ to $C_{22}$ carbon chain even after 6 shampoos.

Unless otherwise noted, the procedure used to treat the hair and measure the Curl Droop is as follows: Hair swatches (2 g., 6.5-7.5 in.) were treated with a solution of film former/Xylose (0.5 g solution/kg of hair) then blow dried. The hair swatches were then heated with a flat iron for 1 minute and then shampooed with 10% sodium laureth sulfate (SLES). The treatment was repeated up to 8 times, as indicated. The hair swatches were then styled with a curling iron for 30 seconds and placed in a humidity chamber at 90% relative humidity to measure the Curl Droop for the heat activated test (Examples 1 through 8). For the durability test (Example 9), the hair swatches were shampooed up to 6 times then styled and placed in a humidity chamber. As the curl slowly relaxed in the humidity chamber, the length of the hair swatches was measured every minute (up to 15 minutes).

The Curl Droop was calculated as:

$$[(L_o-L_t)/(L_o-L_i)] \times 100$$

Where:
$L_o$ represents the original length of fully extended hair
$L_t$ represents the length of the hair at time t in the humidity chamber
$L_i$ represents the initial length of the hair at time 0 in the humidity chamber (i.e., after styling with a curling iron for 30 seconds)
A higher Curl Droop represents a better curl retention.

EXAMPLES 4-7

Examples 4 through 7 show the usefulness of cationic polymers as the at least one film forming agent in the compositions of the present invention as well as the compositions used in the methods of the present invention.

EXAMPLE 4

Heat Activated Styling with Polyquaternium-16

Following the above procedure, bleached hair was treated 8 times with either a solution comprising 6% (active) polyquaternium-16 without xylose (Composition (a)) or a solution comprising 6% (active) polyquaternium-16 and 1% xylose (Composition (b)). Polyquaternium-16 is a polymeric quaternary ammonium salt formed from methylvinylimidazolium chloride and vinylpyrrolidone. The results are shown in Table 1.

TABLE 1

Curl Droop of Hair Treated with Polyquaternium-16

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 66 | 44 | 35 | 26 | 19 | 16 | 16 | 16 | 15 | 14 | 9 | 9 | 9 | 9 | 9 |
| (b) | 100 | 97 | 83 | 74 | 51 | 47 | 35 | 31 | 31 | 24 | 23 | 23 | 22 | 22 | 22 | 22 |

EXAMPLE 5

Heat Activated Styling with Polyquaternium-46

Following the above procedure, normal brown hair was treated 8 times with either a solution comprising 6% (active) polyquaternium-46 without xylose (Composition (a)) or a solution comprising 6% (active) polyquaternium-46 and 1% xylose (Composition (b)). Polyquaternium-46 is a polymeric quaternary ammonium salt prepared by reaction of vinylcaprolactam and vinylpyrrolidone with methylvinylimidazolium methosulfate. The results are shown in Table 2.

TABLE 2

Curl Droop of Hair Treated with Polyquaternium-46

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 68 | 47 | 41 | 26 | 15 | 8 | 8 | 6 | 6 | 6 | 6 | 4 | 4 | 4 | 4 |
| (b) | 100 | 94 | 90 | 74 | 58 | 47 | 41 | 39 | 39 | 38 | 37 | 37 | 35 | 35 | 35 | 35 |

EXAMPLE 6

Heat Activated Styling with Polyquaternium-44

Following the above procedure, bleached hair was treated 8 times with either a solution comprising 6% (active) polyquaternium-44 without xylose (Composition (a)) or a solution comprising 6% (active) polyquaternium-44 and 1% xylose (Composition (b)). Polyquaternium-44 is a polymeric quaternary ammonium salt prepared by reaction of vinylpyrrolidone and quaternized imidazoline monomer. The results are shown in Table 3.

TABLE 3

Curl Droop of Hair Treated with Polyquaternium-44

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 88 | 82 | 74 | 60 | 44 | 43 | 39 | 35 | 29 | 24 | 21 | 19 | 19 | 19 | 19 |
| (b) | 100 | 100 | 99 | 94 | 82 | 69 | 63 | 57 | 46 | 39 | 39 | 39 | 34 | 34 | 34 | 34 |

EXAMPLES 7 AND 8

Examples 7 and 8 show the usefulness of nonionic water-soluble polymers as the at least one film forming agent in the compositions of the present invention as well as the compositions used in the methods of the present invention.

EXAMPLE 7

Heat Activated Styling with Corn Starch

Following the above procedure, bleached hair was treated 8 times with either a solution comprising 6% (active) Corn Starch Modified without xylose (Composition (a)) or a solution comprising 6% (active) Corn Starch Modified and 1')/0 xylose (Composition (b)). Corn Starch Modified is prepared by the reaction of corn starch and polyvinylpyrrolidone. The results are shown in Table 4.

TABLE 4

Curl Droop of Hair Treated with Corn Starch

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 97 | 96 | 91 | 89 | 86 | 80 | 78 | 70 | 66 | 56 | 43 | 43 | 32 | 27 | 25 |
| (b) | 100 | 93 | 93 | 92 | 92 | 90 | 90 | 87 | 83 | 73 | 64 | 62 | 62 | 56 | 55 | 55 |

EXAMPLE 8

Heat Activated Styling with Corn Starch

Following the above procedure, normal brown hair was treated 8 times with either a solution comprising 6% (active) PVPNA Copolymer without xylose (Composition (a)) or a solution comprising 6% (active) PVPNA Copolymer and 1% xylose (Composition (b)). PVPNA Copolymer is a copolymer of vinyl acetate and vinylpyrrolidone. The results are shown in Table 5.

TABLE 5

Curl Droop of Hair Treated with PVP/VA Copolymer

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 94 | 86 | 73 | 71 | 60 | 56 | 54 | 44 | 43 | 35 | 27 | 21 | 21 | 21 | 21 |
| (b) | 100 | 92 | 86 | 77 | 75 | 71 | 70 | 65 | 63 | 62 | 58 | 56 | 52 | 52 | 52 | 52 |

EXAMPLES 9-11

Examples 9 through 11 show the usefulness of anionic polymers as the at least one film forming agent in the compositions of the present invention as well as the compositions used in the methods of the present invention.

EXAMPLE 9

Heat Activated Styling with VA/CrotonatesNinyl Neodecanoate Copolymer

Following the above procedure, bleached hair was treated 4 times with either a solution comprising 6% (active) VA/CrotonatesNinyl Neodecanoate Copolymer without xylose (Composition (a)) or a solution comprising 6% (active) VA/CrotonatesNinyl Neodecanoate Copolymer and 1% xylose (Composition (b)). VA/CrotonatesNinyl Neodecanoate Copolymer is formed from vinyl acetate, crotonic acid and vinyl neodecanoate monomers. The polymer was neutralized to 100% neutralization with AMP (amino methylpyridine). The results are shown in Table 6.

TABLE 6

Curl Droop of Hair Treated with VA/Crotonates/Vinyl Neodecanoate Copolymer

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 81 | 71 | 61 | 41 | 41 | 39 | 33 | 29 | 27 | 25 | 25 | 25 | 25 | 25 | 25 |
| (b) | 100 | 98 | 98 | 96 | 95 | 95 | 94 | 92 | 88 | 88 | 83 | 81 | 80 | 79 | 79 | 79 |

EXAMPLE 10

Heat Activated Styling with Acrylates/C1-2 Succinates Hydroxyacrylates Copolymer Following the above procedure, bleached hair was treated 8 times with either a solution comprising 6% (active) Acrylates/C1-2 Succinates Hydroxyacrylates Copolymer without xylose (Composition (a)) or a solution comprising 6% (active) Acrylates/C1-2 Succinates Hydroxyacrylates Copolymer and 1% xylose (Composition (b)). Acrylates/C1-2 Succinates Hydroxyacrylate4 Copolymer is formed from acrylic acid, acrylates, hydroxyacrylates and succinic acid. The polymer was neutralized to 100% neutralization with AMP. The results are shown in Table 7.

TABLE 7

Curl Droop of Hair Treated with Acrylates/C1-2 Succinates Hydroxyacrylates Copolymer

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 52 | 44 | 27 | 21 | 12 | 11 | 11 | 9 | 3 | 3 | 2 | 0 | 0 | 0 | 0 |
| (b) | 100 | 94 | 90 | 78 | 62 | 60 | 57 | 41 | 35 | 33 | 33 | 33 | 33 | 33 | 31 | 31 |

EXAMPLE 11

Heat Activated Styling with Acrylates Copolymer

Following the above procedure, normal brown hair was treated 8 times with either a solution comprising 6% (active) Acrylates Copolymer without xylose (Composition (a)) or a solution comprising 6% (active) Acrylates Copolymer and 1% xylose (Composition (b)). Acrylates Copolymer is a copolymer of two or more monomers chosen from acrylic acid, methacrylic acid and simple esters thereof. The polymer was neutralized to 100% neutralization with AMP. The results are shown in Table 8.

TABLE 8

Curl Droop of Hair Treated with Acrylates Copolymer

| | Time (minutes) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| (a) | 100 | 92 | 88 | 74 | 73 | 59 | 52 | 50 | 46 | 34 | 11 | 11 | 11 | 11 | 11 | 11 |
| (b) | 100 | 96 | 90 | 86 | 81 | 77 | 76 | 58 | 58 | 52 | 52 | 52 | 52 | 52 | 52 | 52 |

EXAMPLE 12

Heat Activated Durability with Corn Starch

Following the procedure for durability testing, bleached hair was treated 8 times with a solution comprising 6% (active) Corn Starch Modified either without xylose or with 1% xylose. The Curl Droop at 15 minutes was measured at the indicates times. The results are shown in Table 9.

TABLE 9

Curl Droop of Hair Treated with Corn Starch Modified After Various Numbers of Shampoos

| Solution Comprising 6% (active) Corn Starch Modified; Time of Measurement of Curl Droop | Curl Droop After 15 Minutes in 90% Relative Humidity |
|---|---|
| Without xylose; after treatment (no shampoos) | 15 |
| With 1% xylose; after treatment (no shampoos) | 31 |
| Without xylose; after 2 shampoos | 10 |
| With 1% xylose; after 2 shampoos | 18 |
| Without xylose; after 6 shampoos | 0.1 |
| With 1% xylose; after 6 shampoos | 4 |

The data showed that hair treated with at least one film forming agent (Corn Starch Modified), at least one sugar chosen from $C_3$ to $C_5$ monosaccharides (xylose) and heat had a higher curl retention than hair treated with at least one film forming agent (Corn Starch Modified) and heat but without at least one sugar chosen from $C_3$ to $C_5$ monosaccharides (xylose) even after 6 shampoos.

EXAMPLE 13

The following procedure was used to treat the hair and measure the Curl Droop: Hair swatches (2 g., 6.5-7.5 in.) were treated with a solution containing 6% Corn Starch Modified and 1% Glucosamine (0.5 g solution/g of hair) then blow dried. The hair swatches were then heated with a flat iron for 1 minute and then shampooed with 10% sodium laureth sulfate (SLES). The treatment was repeated up to 8 times, as indicated. The treated hair swatches were shampooed 2, 4, and 6 times, then styled with a curling iron for 30 seconds and placed in a humidity chamber at 90% relative humidity to measure the Curl Droop. As the curl slowly relaxed in the humidity chamber, the length of the hair swatches was measured every minute (up to 15 minutes).

The Curl Droop was calculated as explained previously.

TABLE 1

Curl Droop of Hair Treated with Corn Starch Modified

| Solution Comprising 6% (active) Corn Starch Modified | 0 minutes | 5 minutes | 10 minutes | 15 minutes |
|---|---|---|---|---|
| Without glucosamine, after treatment | 100 | 85 | 75 | 62 |
| With glucosamine, after treatment | 100 | 88 | 76 | 65 |
| Without glucosamine, after 2 shampoos | 100 | 83 | 68 | 37 |
| With glucosamine, after 2 shampoos | 100 | 85 | 72 | 40 |
| Without glucosamine, after 4 shampoos | 100 | 81 | 62 | 27 |
| With glucosamine, after 4 shampoos | 100 | 83 | 71 | 32 |
| Without glucosamine, after 6 shampoos | 100 | 77 | 47 | 13 |
| With glucosamine, after 6 shampoos | 100 | 80 | 66 | 19 |

The data showed that hair treated with at least one film forming agent (Corn Starch Modified), at least one compound comprising at least one $C_5$ to $C_7$ saccharide unit substituted with at least one amino group (glucosamine) and heat had a higher curl retention than hair treated with at least one film forming agent (Corn Starch Modified) and heat but without at least one compound comprising at least one $C_5$ to $C_7$ saccharide unit substituted with at least one amino group even after 6 shampoos.

What is claimed is:

1. A composition for durable non-permanent shaping or durable retention of a non-permanent shape of least one keratinous fiber comprising:
    (a) from 0.1 to 10% by weight of the composition of a film forming cationic polymer, a film forming nonionic polymer or a film forming anionic polymer selected from the group consisting of:
        (i) a polymer derived from (1) corn starch and (2) polyvinylpyrrolidone;
        (ii) a copolymer derived from (1) vinyl acetate and (2) vinylpyrrolidone,
        (iii) a polymer derived from (1) vinyl acetate, (2) crotonic acid and (3) vinyl neodecanoate;
        (iv) a polymer derived from (1) acrylic acid, (2) an acrylate, (3) a hydroxyacrylate, and (4) succinic acid;
        (v) a polymer derived from at least two different monomers selected from the group consisting of acrylic acid, methacrylic acid, an ester of acrylic acid, and an ester of methacrylic acid;
        (vi) polyquaternium-16;
        (vii) polyquaternium-46;
        (viii) polyquaternium-44;
    and
    (b) from 0.1 to 5% by weight of the composition of a saccharide type compound chosen from $C_3$ to $C_5$ monosaccharide, optionally substituted with at least one $C_1$ to $C_{22}$ carbon chain, and a compound comprising at least one $C_5$ to $C_7$ saccharide unit substituted with at least one amino group;
    wherein said at least one film forming cationic polymer, film forming nonionic polymer or film forming anionic polymer and said saccharide type compound are present in an amount effective to impart a durable non-permanent shape to said at least one keratinous fiber or to durably retain a non-permanent shape of said at least one keratinous fiber.

2. The composition according to claim 1, comprising a cationic film forming polymer and wherein said cationic film forming polymer is polyquaternium-16, polyquaternium-46 or polyquaternium-44.

3. The composition according to claim 1, comprising a nonionic film forming polymer and wherein said nonionic film forming polymer is (i) a polymer derived from (1) corn starch and (2) polyvinylpyrrolidone; or (ii) a copolymer derived from (1) vinyl acetate and (2) vinylpyrrolidone.

4. The composition according to claim 1, comprising the $C_3$ to $C_5$ monosaccharide, which is selected from the group consisting of pentose, tetrose, triose, furanose, and a derivative of $C_3$ to $C_5$ monosaccharide selected from the group consisting of a hemiacetal compound of $C_3$ to $C_5$ monosaccharide, and a hemiketal compound of $C_3$ to $C_5$ monosaccharide.

5. The composition according to claim 1, comprising said compound comprising at least one $C_5$ to $C_7$ saccharide unit and that is selected from the group consisting of pentosamine, hexosamine and heptosamine.

6. The composition according to claim 1, further comprising an additional sugar different from said saccharide type compound.

7. The composition according to claim 6, wherein said additional sugar is selected from the group consisting of allose, altrose, glucose, mannose, gulose, idose, galactose, talose, sorbose, psicose, fructose, and tagatose.

8. The composition according to claim 6, wherein said additional sugar is present in said composition in an amount ranging from 0.01% to 10% by weight relative to the total weight of the composition.

9. The composition according to claim 1, which is in the form of a liquid, oil, paste, stick, dispersion, emulsion, lotion, gel, or cream.

10. The composition according to claim 1, further comprising at least one additive selected from the group consisting of from anionic surfactant, cationic surfactant, nonionic surfactant, amphoteric surfactant, fragrance, penetrating agent, antioxidants, sequestering agent, opacifying agent, solubilizing agent, emollient, colorant, screening agent, preserving agent, protein, vitamin, silicone, thickening polymer, plant oil, mineral oil, and synthetic oil.

11. A method for durable non-permanent shaping of at least one keratinous fiber or for durable retention of a non-permanent shape of at least one keratinous fiber comprising: applying to said at least one keratinous fiber the composition according to claim 1; heating said at least one keratinous fiber; wherein said composition is applied prior to said heating or during said heating.

12. A kit for protecting at least one keratinous fiber from extrinsic damage or for repairing at least one keratinous fiber following extrinsic damage said kit comprising at least one compartment, wherein said at least one compartment comprises the composition according to claim 1.

13. The composition according to claim 1, wherein (b) is xylose.

* * * * *